US005610178A

United States Patent [19]

Zeeck et al.

[11] Patent Number: 5,610,178

[45] Date of Patent: Mar. 11, 1997

[54] MACROLIDES AND THE USE THEREOF

[75] Inventors: Axel Zeeck, Göttingen; Kai U. Bindseil, Rheinfelden; Claudia Boddien, Göttingen, all of Germany

[73] Assignee: Ciba-Geigy Corporation, Tarrytown, N.Y.

[21] Appl. No.: 287,984

[22] Filed: Aug. 9, 1994

[30] Foreign Application Priority Data

Aug. 16, 1993 [CH] Switzerland ............................ 2435/93

[51] Int. Cl.$^6$ ....................... A61K 31/335; C07D 313/00

[52] U.S. Cl. ............................................ 514/450; 549/271

[58] Field of Search ............................. 514/450; 549/271

[56] References Cited

FOREIGN PATENT DOCUMENTS

05059046-A 3/1993 Japan .

WO91/06296 5/1991 WIPO .

OTHER PUBLICATIONS

Drose, S., et al., "Inhibitory Effect of Modified Balfilomycins and Concanamycins on P– and V–Type Adenosinetriphosphatases", *Biochemistry*, 32(15): 3902–3906 (1993).

Kinashi, H., et al., "Structure of Concanamycin A", *Tetrahedron Letters*, 22(39):3861–3864 (1981).

Kinashi, H., et al., "Isolation and Characterization of Concanamycins A, B and C", *J. Antibiotics*, 37(11):1333–1343, 1984.

Nakai, H. et al., Abstract, "Structure of Concanamycin A Pentahydrate", *Acta Cryst.*, C48:1519–1521 (1992).

Westley, J. W., et al., "The Structure and Absolute Configureation of the 18–Membered Macrolide Lactone Antibiotic X–4357B (Concanamycin A)", *J. Antibiotics*, 37(12):1738–1740 (1984).

Woo, J–T., et al., "Isolation, Characterization and Biological Activities of Concanamycins as Inhibitors of Lysosomal Acidification", *J. Antibiotics*, 45(7):1108–1116 (1992).

*Primary Examiner*—Ba K. Trinh

*Attorney, Agent, or Firm*—James Scott Elmer; Henry P. Nowak

[57] ABSTRACT

Compounds of the formula (I)

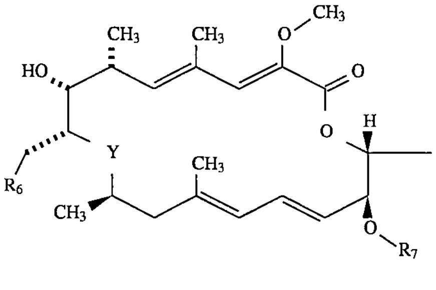

-continued

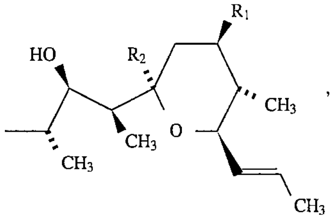

, wherein $R_1$ is hydroxy, 2-hydroxyethoxy, $C_1$–$C_4$alkoxy, $C_1$–$C_4$alkanoyloxy, halogen, amino, azido, a keto, p-nitrobenzenesulfonyl or a pyranyloxy group of the formula

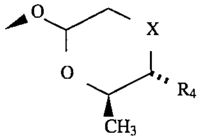

wherein X is a group of the formula

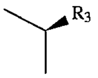

or

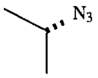

wherein $R_3$ is hydroxy, $C_1$–$C_4$alkanoyloxy or organic sulfonyloxy, and $R_4$ is hydroxy or carbamoyloxy, $R_2$ is hydrogen, hydroperoxy, hydroxy or methoxy, Y is a group of the formula

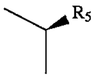

or

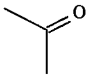

wherein $R_5$ is hydroxy or $C_1$–$C_4$alkanoyloxy, and $R_6$ and $R_7$ each independently of the other is hydrogen or methyl, are suitable for the preparation of a medicament for the prophylaxis and treatment of diseases that respond to the inhibition of the osteoclast proton pump.

24 Claims, No Drawings

MACROLIDES AND THE USE THEREOF

The invention relates to novel concanamycin compounds and to the use of concanamycin compounds in the prophylactic and therapeutic treatment of the human and animal body.

In the human and animal body there is a dynamic equilibrium between the continuous absorption of old bone tissue by osteoclasts and the continuous regeneration of bone by osteoblasts. In the healthy organism, bone absorption and regeneration are closely linked and the total bone mass thus remains constant. In osteotropic diseases, such as osteopenia, absorption exceeds regeneration, leading to a real loss of bone tissue. Osteoclast cells are located in lacunae on the surface of bones and their absorbing activity consists in acidifying by proton secretion the extracellular compartment between bone and osteoclast membrane. The resulting low pH value leads to demineralisation of the bone and activates lysosomal enzymes which then break down the collagen matrix that is released.

Studies of the mechanism responsible for the acidification have revealed that an enzyme located in the osteoclast membrane, an ATP-dependent proton pump (or $H^{30}$-ATPase), especially the osteoclast proton pump, plays a decisive role in the formation and maintenance of the pH gradient through that membrane. The osteoclast proton pump belongs to the multimeric vacuolar class of $H^{30}$-ATPase enzymes which are to be found in the membranes of a large number of intracellular vacuoles (e.g. lysosomes, clathrin-coated vesicles and chromaffin granules). Inhibition of the osteoclast proton pump and, consequently, of the acidification process, is one method of preventing the loss of bone tissue in osteoporosis and other osteopenial diseases.

The present Application relates to the provision of inhibitors of the osteoclast proton pump and hence to pharmaceutical compositions suitable for the treatment of diseases that are characterised by a loss of bone tissue.

The concanamycins A, B and C, which are macrolide antibiotics obtainable from *Streptomyces spec.*, are known to be potent inhibitors of vacuolar $H^+$-ATPase enzymes (S. Dr öse et al., Biochemistry 32 (1993) 3902–3906). Since vacuolar $H^+$-ATPase enzymes are vital for numerous intracellular functions, inhibitors of that class of enzymes would be expected to have a high cytotoxicity. Surprisingly, it has now been found that certain concanamycin compounds are highly active and extremely specific inhibitors of the osteoclast proton pump ("OPPIs"), i.e. OPPIs having no measurable cytotoxity (vacuolar $H^+$-ATPase enzymes are relatively unaffected) and having a wide range of therapeutic uses. The known concanamycins A, B and C are characterised by the following structure:

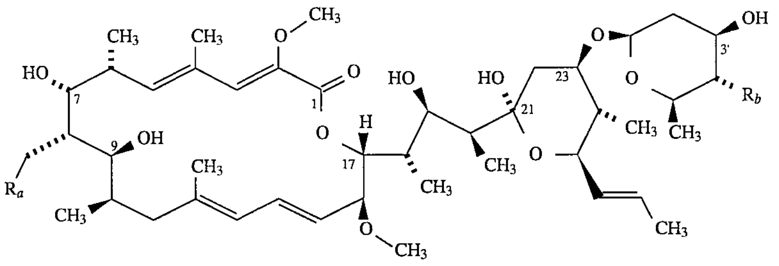

concanamycin A: $R_a$=$CH_3$; $R_b$=O—C(=O)—$NH_2$
concanamycin B: $R_a$=H; $R_b$=O—C(=O)—$NH_2$
concanamycin C: $R_a$=$CH_3$; $R_b$=OH.

The invention relates to the use of compounds of formula (I)

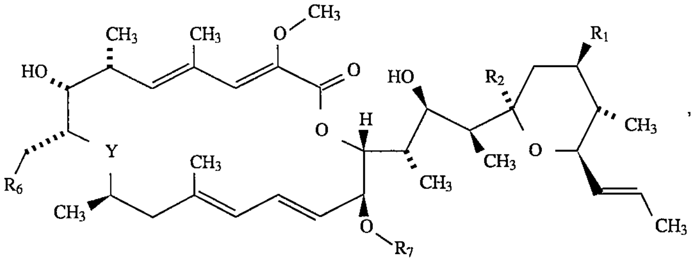

, wherein $R_1$ is hydroxy, 2-hydroxyethoxy, $C_1$–$C_4$alkoxy, $C_1$–$C_4$alkanoyloxy, halogen, amino, azido, keto, p-nitrobenzenesulfonyl or a pyranyloxy group of the formula

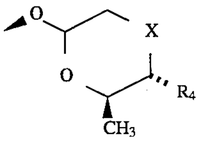

wherein

X is a group of the formula

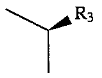 or 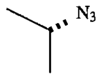

wherein $R_3$ is hydroxy, $C_1$–$C_4$alkanoyloxy or organic sulfonyloxy, and $R_4$ is hydroxy, $C_1$–$C_4$alkanoyloxy or carbamoyloxy, $R_2$ is hydrogen, hydroperoxy, hydroxy, $C_1$–$C_4$alkoxy; preferably hydrogen, hydroxy or methoxy, Y is a group of the formula

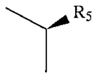 or 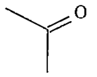

wherein $R_5$ is hydroxy or $C_1$–$C_4$alkanoyloxy, and $R_6$ and $R_7$ are each independently of the other hydrogen or preferably methyl, in the preparation of a medicament that is suitable for the prophylaxis and treatment of diseases that respond to the inhibition of the osteoclast proton pump.

$C_1$–$C_4$Alkoxy is, for example, ethoxy or especially methoxy. $C_1$–$C_4$Alkanoyloxy is, for example, formyloxy, propionyloxy or especially acetoxy. Organic sulfonyloxy is, for example, $C_1$–$C_4$alkanesulfonyloxy, such as methanesulfonyloxy, or benzenesulfonyloxy that is unsubstituted or mono-substituted by $C_1$–$C_4$alkyl, such as methyl, halogen, such as chlorine or bromine, or by nitro, for example 4-nitrobenzenesulfonyloxy.

If $R_1$ is a keto group, the bond between $C_{23}$ and the oxygen is a double bond.

The term halogen stands for fluorine, chlorine, bromine or iodine, especially for chlorine or bromine.

Preference is given to the use of those compounds of formula (I) wherein $R_1$ is hydroxy, methoxy, $NH_3$, chlorine, bromine, a keto, p-nitrobenzenesulfonyl or a pyranyloxy group of the formula

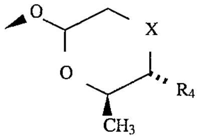

wherein $R_4$ is hydroxy, acetoxy or carbamoyloxy and

X is a group of the formula

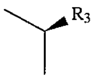 or 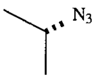

wherein $R_3$ is hydroxy, acetoxy, or benzenesulfonyloxy that is unsubstituted or mono-substituted by $C_1$–$C_4$alkyl, halogen or by nitro, $R_2$is hydrogen or hydroxy, Y is a group of the formula

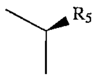 or 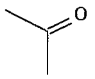

wherein $R_5$ is hydroxy or acetoxy and $R_6$ is methyl.

Special preference is given to the use of compounds of formula (I) wherein $R_1$ is hydroxy, methoxy, azido, chlorine, a keto, p-nitrobenzenesulfonyl or a pyranyloxy group of the formula

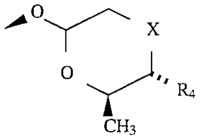

wherein $R_4$ is hydroxy or carbamoyloxy and

X is a group of the formula

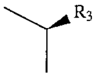

wherein $R_3$ is hydroxy or acetoxy, $R_2$ is hydrogen or hydroxy, and

Y is a group of the formula

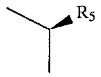

and $R_5$ is hydroxy or acetoxy.

The invention relates especially to the use of concanamycin A, concanamycin C, concanolide A, 21-deoxy-concanolide A, 23-O-methyl-concanolide A, 3', 9-di-O-acetyl-concanamycin A, 16-demethyl-21-deoxyconcanolide A, 21,23-dideoxy-23-epi-azidoconcanolide A, 23-O-(p-nitrobenzenesulfonyl)-21-deoxyconcanolide A, 21-deoxyconcanolide A-23-ketone, 21-deoxyconcanolide A-9,23-diketone, deoxyconcanamycin A and/or 21,23-dideoxy-23-epi-chloroconcanolide A.

The known and the novel compounds of formula (I) have valuable pharmacological properties and can be used for the prophylaxis and treatment of diseases that respond to the inhibition of the osteoclast proton pump. Such diseases, which are characterised by an increased loss of bone tissue, are, for example, primary osteoporosis (juvenile, idiopathic, congenital, postmenopausal (Type 1) and involutional (Type 2)) and secondary osteopenia (associated with or caused by malignant tumours, renal insufficiency, endocrinopathy, malabsorption syndrome, diseases of the liver, immobilisation, arthropathy and iatrogenic diseases).

In order to determine the inhibitory activity, clathrin-coated vesicles from bovine brain (which contain a vacuolar $H^+$-ATPase) are used as the enzyme source (see Xie et al., Methods in Enzym. (1988) 157, 634–646). The cytotoxicity of the compounds studied is determined using confluent cultures of mouse 3T3 fibroblasts and XTT tetrazolium dye (in accordance with Roehm et at., J. Immunol. Methods (1991) 142, 257–265). The compounds that can be used according to the invention are potent inhibitors of the $H^+$-ATPase proton pump, with $IC_{50}$ values in the submicromolar range (approx. 0.5–15 nanomolar) at a cytotoxicity ($IC_{50}$) in the micromolar range (approx. 2-micromolar). The therapeutic utility of the compounds is found from a comparison of the inhibitory activity determined in the $H^+$-ATPase enzyme test and the cytotoxicity test. The compounds that can be used according to the invention have a ratio of $IC_{50}$ (μM, cytotoxicity test): $IC_{50}$ (μM, $H^+$-ATPase enzyme test) of more than 500 and thus have a pronounced inhibiting effect on vacuolar $H^+$-ATPase enzymes and low cytotoxicity. The compounds that can be used according to the invention also inhibit bone absorption in the mouse calvaria test (see Reynolds in: Ball et al. (1976), Organic Culture in Biomedical Research, Cambridge University Press, 355–366). The $IC_{50}$ values in the mouse calvaria test are <0.3 μM.

The medicaments prepared using the compounds of formula (I) are especially in the form of pharmaceutical compositions that are suitable for the prophylactic and therapeutic treatment of the human or animal body, especially in the case of the diseases mentioned above. Those pharmaceutical compositions comprise an effective amount, especially an amount effective in the prophylaxis or treatment of one of the above-mentioned diseases, of the active ingredient together with pharmaceutically acceptable carriers that are suitable for topical application or enteral, for example rectal or oral, or parenteral, for example transdermal, subcutaneous or intravenous, administration and may be inorganic or organic, solid or liquid. The oral dosage form is preferred. In the prophylaxis and treatment of diseases that respond to the inhibition of the osteoclast proton pump, in a warm-blooded animal, a prophylactically or therapeutically effective, osteoclast-proton-pump-inhibiting dose of a compound of formula (I) is administered to the warm-blooded animal. The dose of active ingredient and the nature of the treatment (mode of administration: continuous, intermittent, cyclic) depends inter alia on the nature of the disease, the nature and size of the species to be treated, the defensive condition of the organism and the mode of administration. For example, the daily dose administered to a warm-blooded animal having a body weight of approximately 70 kg is from approximately 0.5 mg to approximately 1500 mg, especially from approximately 5 mg to approximately 500 mg, preferably from approximately 10 mg to approximately 300 mg, of a compound of formula (I). That total daily dose is preferably divided into 1–3 administrations daily. The dose in the case of oral administration is preferably in the upper range of the doses indicated.

For oral administration there are used especially tablets or gelatin capsules that comprise the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol. Tablets can also comprise binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colouring agents, flavourings and sweeteners. The pharmaceutically active compounds of the present invention can also be used in the form of parenterally administrable compositions or in the form of infusion solutions. Such solutions are preferably isotonic aqueous solutions or suspensions which, for example in the case of lyophilised compositions that comprise the active ingredient on its own or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions in question, which, if desired, may comprise further phamacologically active substances, such as antibiotics, are prepared in a manner known per se, for example by means of conventional mixing, granulating, confectioning, dissolving or lyophilising processes, and comprise approximately from 0.01% to 90%, in the case of lyophilisates up to 100%, especially from approximately 0.1% to approximately 50% and more especially from 1% to 30%, active ingredient(s), an active ingredient concentration of less than 1% being especially suitable for compositions to be applied topically.

The invention relates also to the compounds of formula

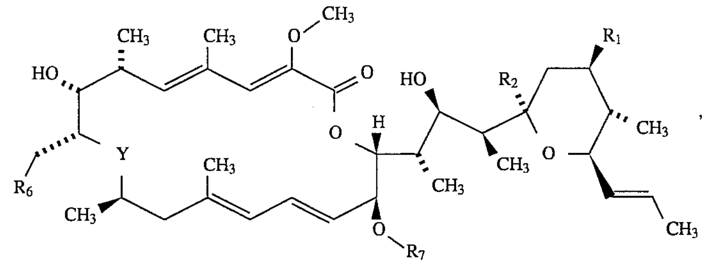

(I)

, wherein $R_6$ and $R_7$ are each independently of the other hydrogen or preferably methyl, and wherein $R_1$ is halogen, amino, azido, keto, p-nitrobenzenesulfonyl or hydroxy, $R_2$ is hydrogen and Y is a group of the formula

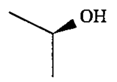

or wherein $R_1$ is halogen, amino, azido, keto, p-nitrobenzenesulfonyl or a pyranyloxy group of the formula

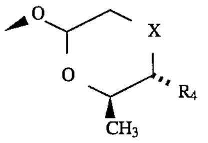

wherein $R_4$ is carbamoyloxy and X is a group of the formula

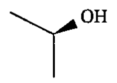

$R_2$ is hydroxy and Y is group of the formula

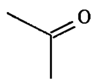

or wherein $R_1$ is halogen, amino, azido, keto, p-nitrobenzenesulfonyl, 2-hydroxyethoxy or a pyranyloxy group of the formula

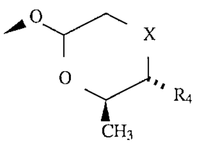

wherein $R_4$ is hydroxy or carbamoyloxy and X is a group of thc formula

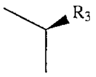 or 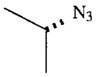

wherein $R_3$ is benzenesulfonyloxy that is unsubstituted or mono-substituted by $C_1$–$C_4$alkyl, halogen or by nitro, $R_2$ is hydrogen, hydroperoxy or hydroxy and Y is a group of the formula

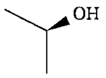

or wherein R is halogen, amino, azido, keto, p-nitrobenzenesulfonyl, $C_1$–$C_4$alkoxy or $C_1$–$C_4$alkanoyloxy, $R_2$ is hydroxy or $C_1$–$C_4$alkoxy, preferably hydroxy or methoxy, and Y is a group of the formula

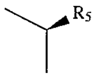

and $R_5$ is $C_1$–$C_4$alkanoyloxy, and to pharmaceutical compositions comprising such compounds of formula (I).

Special preference is given to compounds of formula (I) wherein $R_1$ is hydroxy, azido, p-nitrobenzenesulfonyl, a keto group or chlorine, $R_2$ is hydrogen and Y is a group of the formula

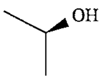

or $R_1$ is a pyranyloxy group of the formula

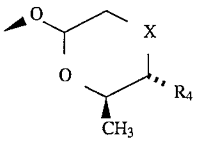

wherein $R_4$ is carbamoyloxy and X is a group of the formula

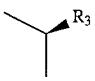 or 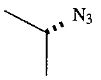

wherein $R_3$ is benzenesulfonyloxy mono-substituted by nitro, $R_2$ is hydroxy and is a group of the formula

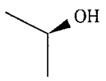

or $R_1$ is acetoxy, $R_2$ is hydroxy and Y is a group of the formula

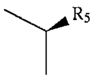

and $R_5$ is acetoxy.

The invention relates especially to 21-deoxy-concanolide A, 16-demethyl-21-deoxyconcanolide A, 21,23-dideoxy-23-epi-azidoconcanolide A, 23-O-(p-nitrobenzene-sulfonyl)-21-deoxyconcanolide A, 21-deoxyconcanolide A-9,23-diketone, deoxyconcanamycin A and/or 21,23-dideoxy-23-epi-chloroconcanolide A.

The compounds of formula (I) are known or can be prepared in accordance with processes known per se. The concanamycins A, B and C that can be used according to the invention and that are also required as starting materials in the preparation of novel compounds of formula (I) according to the invention are obtainable, for example, in accordance with the processes described by Kinashi et al. (J. Antibiotics (1984) 37, 1333–1343) by the fermentation of *Streptomyces diastatochromogenes* S-45 (or of *Streptomyces spec.* Gö 22/15, DSM 8426) and isolation from the mycelium.

Compounds of formula (I) having a keto function in position 9 (Y is a carbonyl group) can be prepared, for example, via the 3',9-diketone. The latter is obtainable from, for example, concanamycin A by mild oxidation (owing to the high instability to hydrolysis), for example with the tetra-n-propylammonium-tetra-oxo-ruthenate(VII) reagent (TPAP). Under mild conditions, for example with sodium borohydride, the 3'-keto group in the diketone can be reduced selectively.

The acylation of free hydroxy groups in positions 9,23 and/or 3' is likewise carried out in a manner known per se using a $C_1$–$C_4$alkanoic acid anhydride (for the introduction of an acetyl group, for example with acetic anhydride) in pyridine. The reaction of concanamycin A or B with acetic anhydride thus yields the 9,3'-di-O-acetyl derivative; using concanamycin C as starting material the 9,3'-di-O-acetyl derivative and the 9,3',4'-tri-O-acetyl derivative are formed. In the deglycosylated concanolides A and B ($R_1$ is hydroxy), the 9,23-di-O-acetyl derivative is obtainable in the same manner. If one of the two hydroxy groups in positions 9 and 23 is blocked, for example, by an ether function, the free hydroxy group is esterified, with the formation of the mono-O-acetyl derivative.

The 3'-hydroxy group in the concanamycins A and C can be selectively O-sulfonated by reaction with corresponding sulfonyl chlorides. In a subsequent reaction the 3'-sulfonyloxy compound can be converted by reaction with an azide, for example sodium azide, into the 3'-epiazido compound.

For the preparation of 21$C_1$–$C_4$alkyl derivatives of the concanamycins, the latter are reacted with the corresponding $C_1$–$C_4$alkanols in the presence of an acid, preferably a Lewis acid, such as $FeCl_3$. Such 21-$C_1$–$C_4$alkyl derivatives of the concanamycins can be converted under acidic conditions (i.e. in the presence of, for example, hydrochloric acid) with sodium cyanoborohydride into the corresponding 2 1-deoxy derivatives.

For the deglycosylation of the concanamycins (and preparation of the concanolides, $R_1$ is hydroxy), the latter are reacted with an organic sulfonic acid, for example p-toluenesulfonic acid, where appropriate in the presence of hydrochloric acid in an aqueous organic solvent (such as water-containing dimethyl sulfoxide or acetonitrile).

Compounds of formula (I) wherein $R_1$ is $C_1$–$C_4$alkoxy or 2-hydroxyethoxy can be prepared, for example, by subjecting a concananycin to acid-catalysed alkanolysis, for example methanolysis or ethanediolysis. p-Toluenesulfonic acid is advantageously used as catalyst. In the presence of Lewis acids, the 21,23-dialkoxy derivatives are also obtainable in that manner.

DEPOSIT OF MICROORGANISMS

The strain Streptomyces spec. Gö 22/15 was deposited on 19.7.1993 at the "Deutsche Sammlung yon Mikroorganismen und Zellkulturen" (German Collection of Microorganisms and Cell Cultures) (DSM) in Brunswick (Germany) under the number DSM 8426.

The Examples that follow illustrate the invention, without limiting the invention in any way.

EXPERIMENTAL SECTION

General Methods

Melting points: The melting and decomposition points were determined using a Reichert hot stage microscope and have not been corrected.

Mass spectra: EI-MS: Varian MAT 731, 70 eV; Finnigan MAT 311 A, 70 eV, high-resolution with perfluorokerosene as comparison compound; FAB-MS: Finnigan MAT 95 A (matrix: α-nitrobenzyl alcohol). DCI-MS: Finnigan MAT 95 A (reactant gas: $NH_3$)

Infrared spectra: IR spectra were measured using a Perkin-Elmer spectrometer, Model 298, and a Perkin-Elmer FT-IR spectrometer, Model 1600; all compounds in the form of compressed KBr disks.

Electron spectra: Kontron Uvikon 860.

Specific rotations: Perkin-Elmer polarimeter, Model 241; the specific rotations are given in $[10^{-1}\ degcm^2\ g^{-1}]$, c in $[g100^{-}\cdot ml^{-1}]$ $^1$H-NMR spectra: Varian XL 200 (200 MHz), Varian VXR 200 (200 MHz), Varian VXR 500 (500 MHz), Bruker AMX 300 (300 MHz). Chemical shifts in $\delta_H$values relative to tetramethylsilane as internal standard; coupling constants (J) in Hz. Abbreviations: s=singlet, d=doublet, t=triplet, dd=double doublet, m=multiplet, br=broad.

$^{13}$C-NMR spectra: Varian XL 200 (50.3 MHz), Varian VXR 200 (50.3 MHz), Varian VXR 500 (125.7 MHz), Bruker AMX 300 (75.5 MHz). Chemical shifts in $\delta_C$ values relative to tetramethylsilane as internal standard.

Column chromatography: silica gel 60 under 0.08 mm (Macherey & Nagel); silica gel 60 0.2–0.05 mm (Macherey & Nagel); silica gel 60 0.04–0.063 mm (Macherey & Nagel); all silica gel columns were operated at p=0.4–0.8 bar excess pressure (flash chromatography); Sephadex LH-20 (Pharmacia).

HPLC: pump: Kontron 414, detector: Kontron 420, mixing chamber: Kontron M 800, Kontron Multiport, data system: Kontron Data System 450; analytical 20 ml feed loop, precolumn: Waters Guard Pak Precolumn Module 5×5 mm with Resolve RP-18 cartridges; column: Kontron 10C18. System: isocratic system, $CH_3CN$/water 65:35, flow rate 4 ml/min, detection at 245 and 285 nm Solvents and chemicals: The solvents for the flash chromatography were distilled in advance; only solvents of Gradient Grade quality (Merck) and doubly distilled water membrane-filtered before use were used for the HPLC. Gradient Grade quality (Merck), where appropriate dried in advance over a suitable drying agent, was generally used for reactions. The standard chemicals used were obtained from Fluka, Aldrich and Merck and used as obtained.

Eluant mixtures for the chromatography:

| | |
|---|---|
| System A: $CHCl_3$/MeOH 8:2 | System B: $CHCl_3$/MeOH 9:1 |
| System C: $CHCl_3$/MeOH 95:5 | System D: EtOAc/n-hexane 4:1 |
| System E: EtOAc/n-hexane 2:1 | System F: EtOAc/n-hexane 1:1 |
| System G: EtOAc/n-hexane 1:2 | System H: EtOAc/n-hexane 1:3 |
| System I: EtOAc/benzene 4:1 | System K: MeOH/$H_2O$ 8:2 (on RP-8) |

Spray reagents: According to Reagenzien Merck, staining reagents for thin-layer and paper chromatography.

Nutrient medium constituents: All the nutrient medium constituents were obtained from Difco.

Shakers and fermenters with aeration setting: Braun Certomat U, Braun Schüttelschrank (shaking cabinet) BS4, Braun Biostat E (5 l; 5 l/min.), Braun Biostat E (15 l; 10 l/min.), Braun Biostat U (50 l; 2 $m^3$/h)

Working-up of reaction mixtures: customary working-up is to be understood as extracting three times with the solvent indicated, combining of the organic phases, drying over $Na_2SO_4$ and subsequent concentration in vacuo using a rotary evaporator.

EXAMPLE 1

Isolation and Characterisation of Concanamycins A, B and C a) Culturing of *Streptomyces sp.* (Gö 22/15) and working-up The strain is maintained on Petri dishes containing M2 agar (10 g/l malt extract, 4 g/l yeast extract, 4 g/l glucose, 25 g/l agar). The plate cultures are inoculated with 48 hour old shaken cultures or with old plate cultures and incubated for about 10 days at 28° C. Typical brown-yellow spots are formed. The aerial mycelium of the strain is white-grey in colour. Unless otherwise indicated, shaken culture fermentations are carried out in 250 ml Erlenmeyer flasks having a baffle and containing 100 ml of M2 nutrient medium or in 1000 ml Erlenmeyer flasks containing 150 ml of M2 nutrient medium.

For culture, inoculation is carried out with agar pieces (1 $cm^2$) from overgrown plate cultures and the flasks are shaken for 72 hours at 28° C. Shaken cultures serving as precultures for bio-reactor fermentations are shaken for 48 hours and then cooled for 24 hours at 4° C.

Bioreactor fermentations arc carried out in a 5 liter or a 50 litre fermenter with M2 nutrient medium (10 g/l malt extract, 4 g/l glucose, 4 g/l yeast extract, 0.15 g/l Niax anti-foam). In the 5 litre fermenter the fermentation is carried out at 220 rpm and with an aeration of 5 l/min; in the 50 litre fermenter it is carried out at 200 rpm and 2 $m^3$/h. For the inoculation, in all cases 10% by volume of 48 hour old, cooled preculture is used. The fermentation is carried out for 72 hours in a pH range of 5.8–7.4, 2N citric acid and 2N NaOH being used for automatic regulation of the pH range. At the end of the fermentation a pH value of 7.4 and heavy citric acid consumption are generally to be observed. If the pH value after 72 hours is below 7.0, the fermentation is extended by 24 hours. The pH value at harvest varies between 6.8 and 7.4 and is adjusted with 0.5N NaOH to 7.4. After the addition of 20% by volume of Celite, the mycelium can be separated off. The filter cake is taken up in acetone and the cells are digested by 15 minutes' treatment in an ultrasound bath or using an Ultraturrax (in the case of fermentation on the 50 litre scale). The batch is filtered again and the organic solvent is evaporated off in vacuo. The process is repeated and the aqueous mycelium extracts are then combined and extracted 2–3 times with EtOAc. In exceptional cases only, the culture filtrate is extracted by shaking 2–3 times with EtOAc.

b.) Isolation of the Concanamycins from Streptomyces Gö 22/15 for Spectroscopic Characterisation and for Biological Test The concanamycins are isolated from 8.06 g of mycelium extract from a 50 liter fermentation in accordance with the following scheme:

- column chromatography on silica gel (gradient $CHCl_3$/methanol 100:0 to 9:1),
- concanamycin C is separated off and purified further by column chromatography on Sephadex LH20 (methanol),
- concanamycins A and B are isolated and separated by MPLC on RP-18 silica gel ($CH_3CN$/water 65:35).

Even the initial chromatography on silica gel (gradient: $CHCl_3$/system C/system B, 8×60 cm) results in chromatographically and spectroscopically highly enriched concanamycin fractions. For the spectroscopic characterisation of the concanamycins, 120 mg of concanamycin C are subjected to gel filtration on Sephadex LH-20 (MeOH, 3×80 cm), after which 109 mg of concanamycin C are obtained in the form of a white amorphous solid. A mixture comprising 113 g of the homologous concanamycins A and B is separated by medium pressure chromatography on RP-18 silica gel (4 ×60 cm, $CH_3CN$-$H_2O$ 65:35) into 84 mg of concanamycin A and 13 mg of concanamycin B.

Concanamycin A: m.p. 163° C.
$C_{46}H_{75}NO_{14}$ (866.10)
$R_f$: 0.19 (RP-18, $CH_3CN$-$H_2O$ 65:35); 0.31 (system B); 0.25 (system I)
$R_t$: 19.1 min (standard HPLC system)
FAB-MS (negative ions): m/e=865 [$M^-$]
FT-IR: ν=3430, 2960, 2880, 1710, 1690, 1620 w, 1450, 1380, 1250, 1110, 1070, 1030, 970, 920, 770 $cm^{-1}$
$[\alpha]_D^{20}$=−18 (c=0.5, MeOH)

Concanamycin B: m.p. 156° C.
$C_{45}H_{73}NO_{14}$ (851.51)
$R_f$: 0.25 (RP-18, $CH_3CN$—$H_2O$ 65:35); 0.31 (system B); 0.25 (system I)
$R_t$: 14.1 min (standard HPLC system)
FAB-MS (negative ions): m/e=851 [$M^-$]
FAB-MS (positive ions): m/e=875 [$M^+$+Na]
DCI-MS (positive ions): m/e=852 (100%, $M^+$); 861 (75%); 870 (26%, M+$NH_4^+$)
$[\alpha]_D^{20}$=−18 (c=0.5, MeOH)

Concanamycin C: m.p. 153° C.
$C_{45}H_{74}O_{13}$ (823.07)
$R_f$: 0.35 (system B); 0.25 (system I)
$R_t$: 16.8 min (standard HPLC system)
FAB-MS (negative ions): m/e=822 [$M^-$]
FT-IR: ν=3430, 2960, 2880, 1690, 1620 w, 1450, 1380, 1250, 1110, 1070, 1030, 970, 920, 760 $cm^{-1}$
$[\alpha]_D^{20}$=−17 (c=0.5, MeOH).

EXAMPLE 2

21-O-Methyl-concanamycin A

In a thoroughly heated 50 ml flask, 800 mg (0.92 mmol) of concanamycin A are dissolved in 19 ml of dry MeOH. 15 mg of $FeCl_3$ (0.09 mmol, 0.1 equiv.) in 1 ml of MeOH are then added and the mixture is stirred for 15 min at room temperature. After the addition of 20 ml of phosphate buffer (pH=7, Merck), the solution is transferred to a 250 ml flask and the organic solvent is carefully removed in vacuo. The remaining aqueous residue is extracted with $CHCl_3$ and, after customary working-up, is filtered on silica gel (system D, 4×10) to yield the title compound. M.p. 141° C.
$C_{47}H_{77}NO_{14}$ (880.13)
$R_f$: 0.31 (system B); 0.58 (system I).
FAB-MS (positive ions): m/e=904[$M^{30}$ +Na](5%); 665(100%)
FAB-MS (negative ions): m/e: 1034[$M^-$+matrix](40%); 880 [$M^-$]
UV (MeOH): $\lambda_{max}$ (ε)=245 (37 000); 283 nm (17 000)
$[\alpha]_D^{20}$=+45.6(c=0.4, MeOH)

EXAMPLE 3

9,3'-Di-O-acetyl-concanamycin A 0.7 ml of acetic anhydride is added to a solution of 78 mg of concanamycin A in 0.8 ml of pyridine and the reaction mixture is stirred for 3 hours at room temperature. When the starting material can no longer be detected (TLC monitoring), the reaction mixture is added dropwise to 10 ml of ice-water and hydrolysed for 30 minutes. When the resulting mixture has been extracted with $CHCl_3$ and then subjected to standard working-up, the resulting crude product is taken up several times in toluene in order to distil off pyridine and acetic acid azeotropically. Purification of the product by column chromatography on silica gel (system E, 3×30 cm) yields the title compound.
$C_{50}H_{79}NO_{16}$ (950.17)
$R_f$: 0.69 (system C) and 0.63 (system E).
FAB-MS (positive ions): m/e=972[$M^+$+Na]
FAB-MS (negative ions): m/e=948[$M^-$]
$[\alpha]_D^{20}$=−28 (c=0.5, $CHCl_3$).

EXAMPLE 4

3'-O-(p-Nitro-benzylsulfonyl)-concanamycin A 35 mg of DMAP (0.29 mmol, 5 equiv.), 0.5 ml of triethylamine and 130 mg of p-nitro-benzene-4-sulfochloride (0.58 mmol, 10 equiv.) are added in succession to a solution of 50 mg (0.058 mmol) of concanamycin A in 5 ml of $CH_2Cl_2$. The reaction mixture is stirred for 2 hours at room temperature. When the conversion is complete, the reaction is stopped by the addition of ice, the phases are separated and the aqueous phase is extracted with $CH_2Cl_2$. Customary working-up and subsequent column chromatography on silica gel (system G, 3×40 cm) yield the title compound in the form of a yellow oil contaminated with approximately 10% unstable 3',9-di-O-(p-nitro-benzylsulfonyl)-concanamycin A.
$C_{52}H_{78}N_2O_{18}S$ (1051.25)
$R_f$: 0.72 (system B); 0.93 (system E).

FAB-MS (negative ions): m/e=1051 [$M^-$]
IR: ν=3150, 2980, 1720, 1690, 1610, 1530 (—$NO_2$), 1350 (—$SO_2$—O—), 1190 (—$SO_2$—O—), 1080 $cm^{-1}$
UV (MeOH): $\lambda_{max}$ (ε)=245(41 000); 284 nm (17 000)
$[\alpha]_D^{20}$=−38(c=0.3, $CHCl_3$).

EXAMPLE 5

3'-Deoxy-epiazido-concanamycin A

A mixture of 96 mg (0.092 mmol) of 3'-O-(p-nitrobenzylsulfonyl)-concanamycin A (Example 4) and 120 mg of $NaN_3$ (1.84 mmol, 20 equiv.) in 10 ml of DMF is stirred for 5 hours at 45° C. After the addition of 15 ml of phosphate buffer (pH=7) the solution is extracted with $CHCl_3$. After customary working-up, the mixture is taken up several times in toluene in order to remove residual DMF by azeotropic distillation (25 mmHg, 50° C.) in a rotary evaporator. Subsequent purification of the crude product by column chromatography on silica gel (system E, 3×30 cm ) yields the title compound in the form of a pale yellow amorphous solid. M.p. 123° C.

$C_{46}H_{74}N_4O_{13}$ (891.11).
$R_f$: 0.74 (system B); 0.74 (system F); 0.18 (system G)
FAB-MS (negative ions): m/e=1144 [$M^-$+matrix]; 890 [$M^-$]
IR: ν=3450, 2980, 2110 (–$N_3$), 1720, 1690, 1620 w, 1250, 1110, 1090 $cm^{-1}$
UV (MeOH): $\lambda_{max}$ (ε)=245 (37 000); 284 nm (16 500)
$[\alpha]_D^{20}$=−17(c=0.6, MeOH)
$^{13}$C-NMR (500 MHz, $CDCl_3$—$CD_3OD$ 2:1, −20° C.): d=6.9 (20-Me); 9.3 (18-Me); 11.7 (10-Me); 13.3 (24-Me); 14.2 (4-Me); 16.2 (12-Me); 16.9 (6-Me); 17.7, 17.8 (C-28 and 6-Me); 21.8, 22.7 (8-Et); 35.0 (C-6); 35.9 (C-10); 36.3 (C-2); 37.0 (C-18); 39.6 (C-22); 41.40, 41.44 (C-20 and C-24); 43.7 (CD-8); 45.4 (C-11); 55.8 (16-OMe); 59.2, 59.3 (16-OMe and C-3); 68.0 (C-5); 70.2 (C-19); 73.5 (C-7); 75.1, 75.5, 75.6, 75.9 (C-17, C-23, C-25 and C-4); 79.7 (C-9); 81.7 (C-16); 94.2 (C-1); 99.7 (C-21); 123.0 (C-13); 126.7 (C-15); 128.3 (C-27); 131.0 (C-26); 131.5, 132.0 (C-3 and C-4); 134.1 (C-14); 141.1, 141.7 (C-2 and C-5); 143.0 (C-12); 156.3 ($OCONH_2$); 166.9 (C-1) ppm.

EXAMPLE 6

23-O-Methyl-conacanolide A 20 mg (0.10 mmol, 0.6 equiv.) of toluene-4-sulfonic acid monohydrate (techn., recrystallised from $CHCl_3$) are added to a solution of 140 mg (0.17 mmol) of concanamycin C in 25 ml of MeOH (analytical grade) and the reaction mixture is stirred for 3 hours at room temperature until the reaction is complete (TLC monitoring), the initially cloudy solution becoming completely clear. The mixture is then transferred to a 250 ml flask containing 5 ml of phosphate buffer (pH=7), the organic solvent is carefully removed in vacuo in a rotary evaporator and the aqueous residue is extracted with $CHCl_3$. Customary working-up, followed by column chromatography on silica gel (system G, 3×30 cm), yields the title compound.

$C_{40}H_{66}O_{10}$ (706.96)
$R_f$: 0.62 (system C); 0.44 (system G)
FAB-MS (negative ions): m/e=707 [$M^-$]
IR: =3460, 2960, 1690, 1610 w; 1440, 1350, 1240, 1100 $cm^{-1}$
UV (MeOH): $\lambda_{max}$ (ε)=245 (40 000); 283 nm (18 000)
$[\alpha]_D^{20}$=+16 (c=0.3, $CHCl_3$).

EXAMPLE 7

21,23-Di-O-methyl-concanolide A

A solution of 140 mg (0.17 mmol) of concanamycin C is reacted in accordance with the general procedure for methanolysis of concanamycins (see Example 6), but with chemicals of technical quality. Completely analogous working-up followed by column chromatography on silica gel (system G, 3×30 cm) yields the title compound in the form of a white amorphous solid. M.p. 97° C.

$C_{41}H_{68}O_{10}$ (720.98)
$R_f$: 0.53 (system C); 0.50 (system G).
FAB-MS (positive ions): m/e=745 [$M^+$+Na]
FAB-MS (negative ions): m/e=721 [$M^-$]; 773 [$M^-$+matrix]
IR: ν=3480, 2960, 1690, 1610 w; 1440, 1350, 1250, 1100 $cm^{-1}$
UV (MeOH): $\lambda_{max}$ (ε)=245 (42 000); 283 nm (18 000)
$[\alpha]_D^{20}$=+9(c=0.3, $CHCl_3$)
$^{13}$C-NMR (125 MHz, $CH_2Cl_2$—$CD_3OD$ 2:1, −20° C.): d=7.5(20-Me); 10.5(18-Me); 12.1 (8-Et); 13.4(24-Me); 14.3 (4-Me); 16.4 (12-Me); 17.1 (6-Me); 18.0 (C-28); 34.5, 35.0, 35.4, 35.9 (C-6, C-10, C-18, C-22); 38.3, 41.3 (C-20 and C-24); 44.3 (C-8); 46.0 (C-11); 46.8 (21-OMe); 56.0 (16-OMe); 56.7 (23-OMe); 60.3 (2-OMe); 70.0 (C-19); 73.6 (C-7) 76.3, 77.3, 79.8, 79.9 (C-9, C-17, C-23, C-25); 82.8 (C-16); 104.2 (C-21); 123.3 (C-13); 127.0 (C-15); 130.5, 130.7, 131.8, 132.6 (C-3, C-4, C-26, C-28); 134.3 (C-14); 141.9 142.1 (C-2 and C-5); 143.4 (C-12); 167.0 (C-1) ppm.

EXAMPLE 8

9-O-Acetyl21,23-di-O-methyl-concanolide A 37 mg (0.051 mmol) of 21,23-di-O-methyl-concanolide A are reacted in accordance with the general procedure for the acetylation of concanamycins (see Example 3). Column chromatography on silica gel (system G,2×20 cm) yields the title compound.

$C_{43}H_7O_{11}$ (763.02).
$R_f$: 0.56 (system G)
FAB-MS (positive ions): m/e=787 [$M^+$+Na]
FAB-MS (negative ions): m/e=763 [$M^-$]
IR: ν=3420, 2960, 1740, 1690, 1620 w; 1450, 1370, 1250, 1100; 1010 $cm^{-1}$
UV (MeOH): $\lambda_{max}$ (ε)=245 (42 000); 283 nm (21 000)
$[\alpha]_D^{20}$=+5 (c=0.5, $CHCl_3$).

EXAMPLE 9

23-O-(2-Hydroxyethyl)-concanolide A 700 mg (0.81 mmol) of concanamycin A are dissolved in a mixture of 50 ml of 1,2-ethanediol, 10 ml of THF and 0.2 ml of 0.5HCl and the reaction mixture is stirred at room temperature. The reaction is discontinued after 18 hours by the addition of 10 ml of phosphate buffer (pH=7) and 190 ml of water and, after customary working-up, extraction is carried out with $CHCl_3$. Column chromatography on silica gel (system E,4×40 cm) yields the title compound.

$C_{41}H_{68}O_{11}$ (736.98)
$R_f$: 0.43 (system B); 0.45 (system E)
IR: ν=3450, 2930, 1720 sh, 1690, 1620 w, 1460, 1250, 1110 $cm^{-1}$
UV (MeOH): $\lambda_{max}$ (ε)=245 (35 000); 283 nm (16 000)
$[\alpha]_D^{20}$=−5 (c=0.3, $CHCl_3$)

EXAMPLE 10

Concanolide A 95 mg (0.50 mmol, 3.5 equiv.) of toluene-4-sulfonic acid monohydrate are added to a solution of 118 mg (0.143 mmol) of concanamycin C in 15 ml of acetonitrile and 3.5 ml of water and the reaction mixture is stirred for 20 hours at room temperature. The mixture is then cooled in an ice-bath to 0° C., 30 ml of saturated $NaHCO_3$ solution are added and the reaction mixture is extracted rapidly with $CHCl_3$. After customary working-up the title compound can be obtained by column chromatography on silica gel (system E, 3×30 cm).

$C_{39}H_{64}O_{10}$ (692.93)
$R_f$: 0.29 (system C); 0.79 (system E); 0.17 (system F)
FAB-MS (negative ions): m/e=693 [$M^-$]
IR: ν=3460, 2960, 1690, 1620 w, 1250, 1100, 960 $cm^{-1}$
UV (MeOH): $\lambda_{max}$ (ε)=245 (32 000); 284 nm (17 000)
$[\alpha]D^{20}$ =+11 (c=0.3, $CHCl_3$).

EXAMPLE 11

9,21-Di-O-acetyl-concanolide A

The title compound is prepared in accordance with the general procedure for the preparation of acetylated concanamycins (see Example 3) from 48 mg (0.070 mmol) of concanolide A. After purification of the crude product by chromatography on silica gel the pure compound is obtained. M.p. 125° C.

$C_{43}H_{68}O_{12}$ (777.01).
$R_f$: 0.54 (system G).
FAB-MS (positive ions): m/e=799 [$M^+$+Na]
FAB-MS (negative ions): m/e=776 [$M^-$]
IR: ν=3450, 2980, 1740, 1690, 1620 w, 1250, 1110 $cm^{-1}$
UV (MeOH): $\lambda_{max}$ (ε)=245 (35 000); 283 nm (16 000)
$[\alpha]_D^{20}$=+7 (c=0.4, $CH_2C_{12}$).

EXAMPLE 12

21-Deoxyconcanamycin A 4 ml of 0.5N HCl are added to a solution of 388 mg (0.44 mmol) of 21-O-methyl-concanamycin A and 193 mg of $NaBH_3CN$ (3.08 mmol, 7 equiv.) in 50 ml of EtOH and the reaction mixture is stirred at room temperature until the starting material can no longer be detected by TLC chromatography. Owing to the similarity in the chromatographic behaviour of the starting material and the product, the TLC monitoring of the course of the reaction proves to be difficult; the product spot can, however, be stained yellow-brown with anisaldehyde/$H_2SO_4$ spray reagent, while the starting material can be stained blue-violet. After 3 hours 60 ml of phosphate buffer (pH=7) are added, EtOH is removed in vacuo and the aqueous solution is extracted with $CHCl_3$. Customary working-up is followed by chromatography on silica gel (system D, 4×40 cm). M.p. 140° C.

$C_{46}H_{75}NO_{13}$ (850.10).
$R_f$=0.31 (system B); 0.54 (system D)
FAB-MS (positive ions): m/e=872 [$M^+$+Na]
IR: ν=3450, 2980, 1710, 1690, 1620 w, 1380, 1250, 1100 $cm^{-1}$
UV (MeOH): $\lambda_{max}$ (ε)=245 (36 500); 283 nm (16 000)
$[\alpha]D^{20}$=−46 (c=1, MeOH)
$^1$H-NMR (300 MHz, CDCl3): d=1.58 (d br, J=6, 3H, 28-$H_3$); 1.80 (s, 3H, 12-Me); (s, 3H, 4-Me); 2.18 (ddd, J=12, 5, 1.5, 1H, 22-$H_{eq}$); 2.70 (m, 1-H, 6-H); 3.22 (m obs, 1-H, 9-H); 3.22 (s, 3H, 16-OMe); 3.55 (s, 3H, 2-OMe); 3.74 (ddd, J=11, 9, 5, 1H, 3-H); 3.83 (dd, J=9, 9, 1H, 16-H); 4.28 (dd, J=9, 9, 1H, 3-H); 4.56 (dd, J=10, 2, 1H, 1-H); 4.88 (s, 2H, $NH_2$); 5.18 (d br, J=10, 1H, 17-H); 5.21 (rid, J=15, 9, 1H, 15-H); 5.31 (ddq, J=15, 8, 2, 1H, 26-H); 5.54 (dq, J=15, 6.5, 1H, 27-H); 5.6–5.7 (s br, 1H, 5-H); 5.77 (d br, J=10, 1H, 13-H); 6.35 (s, 1H, 3-H); 6.51 (dd, J=15, 10, 1H, 14-H) ppm.

EXAMPLE 13

21-Deoxy-concanolide A 500 mg (2.6 mmol, 22.5 equiv.) of toluene-4-sulfonic acid in 3 ml of 1N HCl are added to a solution of 100 mg of 21-deoxyconcanamycin A (0.117 mmol) in 15 ml of MeOH and the reaction mixture is stirred for 48 hours at room temperature. After the addition of 20 ml of phosphate buffer (pH=7) the solvent is removed in vacuo. Standard working-up, followed by column chromatography on silica gel (system E then system D), yields the title compound. M.p. 104° C.

$C_{39}H_{64}O_9$ (676.93).
$R_f$=0.55 (system B); 0.61 (system E); 0.44 (system F)
FAB-MS (positive ions): m/e=833 [$M^+$+matrix]; 699 [$M^+$+Na]
IR: ν=3450, 2960, 1690, 1650 w, 1620 w, 1450, 1380, 1250, 1110 $cm^{-1}$
UV (MeOH): $\lambda_{max}$ (ε)=245 (39 000); 282 nm (17 000)
$[\alpha]_D^{20}$=−23 (c=0.6, MeOH)
$^1$H-NMR (200 MHz, $CDCl_3$): d=1.62 (dd, J=6, 1, 3H, 28-$H_3$); 1.83 (s br, 3H, 12-Me); 1.98 (s br, 3H, 4-Me); 2.78 (m, 1H, 6-H); 3.24 (s, 3H, 16-OMe); 3.58 (s, 3H, 2-OMe); 3.31 (dd, J=10, 8, 1H, 25-H); 3.83 (dd, J=9, 9, 1H, H-16); 5.23 (dd, J=9, 1.5, 1H, 17-H); 5.25 (dd, J=15, 10, 1H, 15-H); 5.33 (ddq, J=15, 8, 1, 1H, 27-H); 5.57 (dq, J=15, 6, 1H, 26-H); 5.80 (d, J=10, 1H, 13-H); 6.38 (s, 1H, 3-H); 6.52 (dd, J=15, 10, 1H, 14-H) ppm.

EXAMPLE 14

Concanamycin A-3',9-diketone 400 mg (0.462 mmol) of concanamycin A are dissolved in 40 ml of dry methylene chloride and 250 mg (4 equiv.) of 4-methylmorpholine 4-oxide monohydrate (Fluka) and 40 mg (0.1 equiv.) of tetrapropylammonium perruthenate (Fluka) are added. The resulting mixture is stirred at room temperature, the initially green colour of the solution gradually changing to black. When the reaction is complete, but at most after 2 hours (there are great variations in the activity of the catalyst), the reaction mixture is separated, without further working-up, by column chromatography on silica gel (system E, 3×30 cm) to yield the title compound. M.p. 170° C.

$C_{46}H_{71}NO_{14}$ (862.07).
$R_f$=0.54 (system B); 0.53 (system E)
FAB-MS (negative ions): m/e=862 [$M^-$]
IR: ν=3450, 2970, 1740, 1690, 1620 w, 1450, 1250, 1100 $cm^{-1}$
UV (MeOH): $\lambda_{max}$ (ε)=245 (34 000); 283 nm (15 000)
$[\alpha]_D^{20}$=−52.0 (c=0.9, $CH_2C_{12}$).

EXAMPLE 15

Concanamycin A-9-ketone

A solution of 126.5 mg (0.146 mmol) of concanamycin A-3',9-diketone in 11 ml of EtOH is cooled to −78° C. After the addition of 38.5 mg (7 equiv.) of $NaBH_4$ the reaction mixture is stirred for 1 hour while maintaining the cooling. The reaction is stopped by the addition of 10 ml of phosphate buffer (pH=7) to the still cold mixture which is then heated to room temperature and extracted with EtOAc. The crude product obtained after customary working-up is purified by column chromatography (EtOAc-n-hexane 3:1) to yield the title compound. M.p. 138° C.

$C_{46}H_{73}NO_{14}$ (864.08).

$R_f$=0.42 (system B); 0.24 (system E)

FAB-MS (negative ions): m/e=863 [$M^-$]

IR: ν=3450, 2970, 1740, 1690, 1620 w, 1450, 1250, 1100 $cm^{-1}$

UV (MeOH): $\lambda_{max}$ (ε)=245 (34 000); 283 nm (15 000)

$[\alpha]_D^{20}$=−43.0 (c=0.4, $CH_2Cl_2$).

EXAMPLE 16

Pharmaceutical Composition

Tablets comprising 20 mg of active ingredient, for example one of the compounds of formula (I) described in the preceding Examples, are prepared in the following composition in customary manner:

| Composition: | |
|---|---|
| active ingredient | 20 mg |
| wheat starch | 60 mg |
| lactose | 50 mg |
| colloidal silica | 5 mg |
| talcum | 9 mg |
| magnesium stearate | 1 mg |
| | 145 mg |

Preparation

The active ingredient is mixed with a portion of the wheat starch, with lactose and colloidal silica and the mixture is forced through a sieve. A further portion of the wheat starch is made into a paste with 5 times the amount of water on a water bath and the powder mixture is kneaded with the paste until a weakly plastic mass is formed.

The plastic mass is pressed through a sieve of 3 mm mesh size and dried and the resulting dried granules are again forced through a sieve. The remaining wheat starch, the talcum and the magnesium stearate are then mixed in and the mixture is compressed to form tablets weighing 145 mg and having a breaking notch.

EXAMPLE 17

21-Deoxyconcanamycin A 5 ml of 0.5N HCl are added to a solution of 500 mg (0.57 mmol) of 21-O-methylconcanamycin A and 258 mg of $NaBH_3CN$ (4.11 mmol, 7 equiv.) in 65 ml of EtOH and the reaction mixture is then stirred at room temperature for 4 hours. The TLC monitoring is effected using RP 8-silica gel plates (Merck) (eluant: $MeOH/H_2O$ 9:2). For working-up, 60 ml of phosphate buffer (pH=7) are added, EtOH is removed in vacuo and the aqueous residue is extracted with $CHCl_3$. Purification is carried out by MPLC chromatography on RP 18-silica gel (eluant: $MeOH/H_2O$ 8:2). The yield is 228 mg (47%), m.p.: 140° C.

$R_f$=0.44 (system K)

EXAMPLE 18 and 19

21-Deoxyconcanolide A and 16-demethyl-21-deoxyconcanolide A 350 mg (1.83 mmol, 3 equiv.) of toluenesulfonic acid monohydrate (recrystallised from $CHCl_3$) are added to a solution of 467 mg of 21-deoxyconcanamycin A (0.55 mmol) in 55 ml of $CH_3CN/H_2O$ (5:1) and the reaction mixture is stirred at 38° C. for 12 hours. For working-up, the reaction mixture is cooled to 0° C. and 50 ml of saturated $NaHCO_3$ solution are added; the organic solvent is removed in vacuo and the aqueous phase is extracted with $CHCl_3$. TLC monitoring on silica gel (eluant: EtOAc/hexane 1:1) revealed two new zones in addition to the starting material at the starting spot. Column chromatography on silica gel (gradient EtOAc/hexane, 1:1 EtOAc) yields 63 mg (22% of the conversion) of 16-demethyl-21-deoxyconcanolide A, 122 mg of 21-deoxyconcanolide A (42% of the conversion) and 105 mg of starting material.

21-Deoxyconcanolide A

M.p.: 122° C.

$C_{39}H_{64}O_9$ (676.93)

$R_f$=0.40 (system F)

FAB-MS (positive ions): m/e=699 [$M^+$+Na]

IR: ν=3450, 2960, 1690, 1650 w, 1620 w, 1450, 1380, 1250, 1110$cm^{-1}$

UV (MeOH): $\lambda_{max}$ (e)=245 (39 000); 282 nm (17 000)

$[\alpha]^{20}{}_D$=−23 (c=0.6, MeOH)

$^1$H-NMR (500 MHz, $CD_2C_{12}/CD_3OD$ 2:1, −20° C.): $\delta_H$=0.78–0.86 (m, 12 H, 20-Me, 18-Me, 8-ethyl-$CH_3$, 24-Me); 0.98 (d, J=7, 3 H, 6-Me); 1.02 (d, J=6.5, 3 H, 10-Me); 1.09–1.18 (m, 4 H, 22β-H, 24 H, 8-ethyl-$CH_2$); 1.42 (ddt, J=11, 8, 3, 1 H, 8-H); 1.60 (dd, J=6.5, 1.5, 3 H, 28-Me); 1.88 (s, 3 H, 12-Me); 1.94 (s, 3 H, 4-Me); 1.97–2.07 (m, 4 H, 11-$H_2$, $_{22}$α-H, 18-H); 2.38(m, 1 H, 10-H); 2.67 (m, 1H, 6-H); 3.12(d, J=10.5, 1 H, 9-H); 3.22 (s, 3 H, 16-OMe); 3.26–2.33 (m, 2 H, 23-H, 25-H); 3.43 (dt, J=10, 0.5, 1 H, 21-H); 3.51 (s, 3 H, 2-OMe); 3.62 (dd, J=10, 1, 1 H, 19-H); 3.67 (dd, J=10, 2.5, 1 H, 7-H); 3.86(dd, J=9, 1 H, 16-H); 5.11 (dq, J=9,0.5, 1 H, 17-H); 5.15(dd, J=15, 9, 1 H, 15-H); 5.28 (ddq, J=15, 8, 1, 1 H, 26-H); 5.56 (dq, J=15, 6.6, 1 H, 27-H); 5.68 (d, J=9.5, 1 H, 5-H); 5.76 (d, J=11, 1 H, 13-H); 6.43 (s, 1 H, 3-H); 6.61 (dd, J=15, 11 1 H, 14-H) ppm.

16-Demethyl-21-deoxyconcanolide A:

M.p.: 87° C.

$C_{38}H_{62}O_9$ (662.90)

$R_f$=0.60 (system F)

FAB-MS (positive ions): m/e=684 [$M^+$+Na]

IR: ν=3449, 2962, 2929, 1711, 1623, 1454, 1374, 1244, 1106, 1016, 970 $cm^{-1}$

UV (MeOH): $\lambda_{max}$ (e)=243 (23 200); 278 nm (13 400)

$[\alpha]^{20}{}_D$=−108.61 (c=0.86, MeOH)

$^1$H-NMR (500 MHz, $CD_2Cl_2/CD_3OD$ 2:1, −20° C.): $\delta_H$=0.86 (m, 3H, 8-ethyl-$CH_3$); 0.90 (d, J=6.5, 3 H, 24-Me); 0.93 (d, J=6.5, 3 H, 10-Me); 0.99 (d, J=7, 3 H, 20-Me); 1.02 (d, J=6.5, 3 H, 18-Me); 1.08 (d, J=6.5, 3 H, 6-Me); 1.10 (m, comp, 8-ethyl-$CH_2$, β-H); 1.15–1.24 (m, 3H, 24-H, 2213-H, 8-ethyl-$CH_2$, α-H); 1.36 (m, 1 H, 8-H); 1.53 (dd, J=16, 9, 1 H, 11β-H); 1.65 (s, 3 H, 12-Me); 1.71 (dd, J=6.6, 1.5, 3 H, 28-Me); 1.79 (m, 1 H, 20-H); 1.86 (d, J=18, 1 H, 11α-H); 1.92 (s, 3 H, 4-Me); 2.08 (dd, J=14, 4, 1 H, 22α-H); 2.18 (m, 1 H, 18-H); 2.24 (m, 1 H, 10-H); 2.63 (m, 1 H, 6-H); 3.12 (dd, J=10, 0.5, 1 H, 9-H); 3.28 (ddd, J=12, 12, 5, 1 H, 23-H); 3.37 (m, 2 H, 21-H, 25-H); 3.56 (s, 3 H, 2-OMe); 3.57 (dd, J=10, 2, 1 H, 7-H); 3.90 (dd, J=9, 1 H, 9-H); 4.59 (dd, J=9, 1 H, 16-H); 5.03 (dd, J=9, 1.5, 1 H, 17-H); 5.38 (m, comp, 1 H, 26-H); 5.43 (dd, J=15, 9, 1 H, 15-H); 5.69 (dq, J=15, 6, 1 H, 27-H); 5.79 (d, J=11, 1 H, 13-H); 5.93 (d, J=10, 1 H, 5-H); 6.30 (dd, J=15, 11, 1 H, 14-H); 6.43 (s, 1 H, 3-H) ppm. $^{13}$C-NMR (125 MHz, $CD_2Cl_2/CD_3OD$ 2:1, −20° C.): $\delta_C$=8.7 (20-Me); 12.5 (10-Me); 13.5 (24-Me); 13.7 (18-Me); 14.6 (4-Me); 17.2 (8-$CH_2$—$\underline{C}H_3$) 18.1 (28-Me); 18.3 (6-Me); 19.3 (12-Me); 25.2 (8$\underline{C}H_2$—$CH_3$); 35.4 (C-10); 36.0 (C-6); 39.1 (C-22); 39.3 (C-20); 39.8 (C-18); 42.8 (C-11); 44.0 (C-24); 45.7 (C-8); 60.2 (2-OMe); 73.6 (C-21); 77.1 (C-9); 77.3 (C-23); 79.1 (C-7); 79.3 (C-16); 81.8 (C-19); 82.5 (C-17); 83.2 (C-25); 121.9 (C-13); 128.4 (C-15); 129.1 (C-16); 129.6 (C-27); 130.9 (C-26); 131.9 (C-3); 132.7 (C-4); 138.7 (C-12); 141.6 (C-5); 142.5 (C-2); 165.7 (C-1) ppm.

EXAMPLE 20

23-O-(p-nitrobenzenesulfonyl)-21-deoxyconcanolide A 179.5 mg (1.5 mmol, 11.3 equiv.) of DMAP, 1.6 ml of triethylamine and 334 mg of p-nitrobenzenesulfochloride (1.5 mmol, 11.3 equiv.) are added in succession to a solution of 85.5 mg of 21-deoxyconcanolide A (0.13 mmol) in 5 ml of $CH_2Cl_2$. The reaction mixture is stirred for 1 hour at 0° C. and the reaction is stopped by the addition of ice. The phases are separated and the aqueous phase is extracted with $CHCl_3$. The organic solvent is removed in vacuo and the reaction mixture is purified by column chromatography on silica gel (eluant: EtOAc/hexane 2:3). Yield: 96.6 mg (85%).

M.p.: 96° C.

$C_{45}H_{67}O_{14}NS$ (878.09)

$R_f$=0.56 (system F)

FAB-MS (negative ions): m/e=859 [$M^-H_2O$]

IR: ν=3485, 2967, 2875, 1696, 1534, 1351, 1248, 1186, 1102, 915 $cm^{-1}$

UV (MeOH): $\lambda_{max}$ (e)=245 (55 700); 278 nm (28 200)

$[\alpha]^{20}_D$=−108.61 (c=0.62, MeOH)

$^1$H-NMR (500 MHz, $CD_2Cl_2/CD_3OD$ 2:1, −20° C.): $\delta_H$ =0.55 (d, J=6.5,3 H,24-Me); 0.73 (d, J=7,3 H, 20-Me); 0.80 (m,6 H,18-Me,8-ethyl-$CH_3$); 0.98 (d, J=7,3 H, 6-Me); 102 (d, J=7,3 H, 10-Me); 1.06 (m, 2 H,8-ethyl-$CH_2$); 1.40–1.49 (m, 3 H, 8-H, 24-H, 22β-H); 1.57 (dd, J=6.6, 1.5, 3 H, 28-Me); 1.68 (m, 1 H, 20-H); 1.80 (s,3 H, 12-Me); 1.93 (s, 3 H, 4-Me); 1.96–2.03 (m, 3 H, 18-H, 11-$CH_2$); 2.16 (m, 1 H, 22α-H); 2.40 (m, 1 H, 10-H); 2.66 (m, 1 H, 6-H); 3.12 (dd, J=10, 0.5, 1 H, 9-H); 3.22 (s, 3 H, 16-OMe); 3.36 (dd, J=10, 8, 1 H, 25-H); 3.43 (m, 1 H, 21-H); 3.50 (s, 3 H, 2-OMe); 3.55 (m, 1 H, 17-H); 3.68 (dd, J=10, 2, 1 H, 19-H); 3.85 (dd, J=9, 1 H, 16-H); 4.42 (m, 1 H, 23-H); 5.17 (comp, 17-H); 5.24 (m, 2H, 26-H, 15-H); 5.55 (dq, J=15, 6.5, 1 H, 27-H); 5.67 (d, J=10, 1 H, 5-H); 5.75 (d, J=11, 1 H, 13-H); 6.41 (s, 1H, 3-H); 6.62 (dd, J=15, 11, 1 H, 14-H); 8.18 (d, J=8.8, 2 H, 3-H); 8.46 (d, J=8.5, 2 H, 2-H) ppm.

$^{13}$C-NMR (125 MHz, $CD_2Cl_2/CD_3OD$ 2:1, −20° C.): $\delta_C$=8.1 (20-Me); 9.7 (18-Me); 12.0 (8-$CH_2$—$\underline{C}H_3$), 13.6 (24-Me); 14.3 (4-Me); 16.5 (12-Me); 17.1 (6-Me); 17.9 (28-Me); 22.0 (10-Me); 23.1 (8-$\underline{C}H_2$—$CH_3$); 35.4 (C.6); 36.1 (C-10); 37.3 (C-22); 37.8 (C-18); 39.7 (C-20); 41.7 (C-24); 44.3 (C-8); 45.9 (C-11); 56.0 (16-OMe); 59.6 (2-OMe); 69.7 (C-7); 73.9(C-19); 76.3(C-21); 76.4(C-17); 79.9(C-9); 82.7(C-16); 82.9(C-25); 87.6(C-23); 123.3 (C-13); 125.1 (2×C-3); 127.1 (C-15); 129.8 (2×C-2); 130.1 (C-27); 130.3 (C-26); 131.7 (C-3); 132.0 (C-4); 134.2 (C-14); 141.6 (C-5); 142.2 (C-2); 143.2 (C-12, C—$SO_3$); 151.2 (C—$NO_2$); 166.7 (C-1) ppm.

EXAMPLE 21

21,23-Dideoxy-23-epoazidoconcanolide A

A mixture of 119 mg of 23-O-(p-nitrobenzenesulfonyl)-21-deoxyconcanolide A (0.13 mmol) and 163 mg (2.5 mmol) of $NaN_3$ in 16.5 ml of DMF is stirred for 45 minutes at 40° C. After the addition of 15 ml of phosphate buffer (pH 7, Merck), the solution is extracted with $CHCl_3$. After customary working-up, the reaction mixture is taken up several times in toluene in order to remove residual DMF by azeotropic distillation (25 mmHg, 50° C.) in a rotary evaporator. There follows column chromatography (EtOAc/-hexane, 1:2), it being possible for 63 mg (69%) of product and 32 mg of starting material to be obtained.

M.p.: 97° C.

$C_{39}H_{63}O_8N_3$ (701.90)

$R_f$=0.43 (system G)

FAB-MS (positive ions): m/e=723 [$M^+$+Na]

IR: ν=3448, 2966, 2930, 2098, 1695, 1622, 1454, 1379, 1249, 1104, 967 $cm^{-1}$

UV (MeOH): $\lambda_{max}$ (ε)=244 (33 400); 282 nm (14 000)

$[\alpha]^{\circ}_D$=108.61 (c=0.62, MeOH)

$^1$H-NMR (500 MHz, $CD_2Cl_2/CD_3OD$ 2:1, −20° C.): $\delta_H$=0.81 (m, 12 H, 24-Me, 8-ethyl-$CH_3$, 18-Me, 20-Me); 0.98 (d, J=7, 3 H, 6-Me); 1.02 (d, J=6.5, 3 H 10-Me); 1.10 (m, 2 H, 8-ethyl-$CH_2$); 1.43 (m, 1 H, 8-H); 1.54 (m, 3 H, 22β-H, 24-H, 20-H); 1.60 (dd, J=6.5, 1.5, 3 H, 28-Me); 1.88 (s, 3 H, 12-Me); 1.94 (s, 3 H, 4-Me); 1.98 (m, 2 H, 11-$CH_2$); 2.04 (m, 2 H, 22α-H, 18-H); 2.39 (m, 1 H, 10-H); 2.67 (m, 1 H, 6-H); 3.11 (d, J=10, 5, 1 H, 9-H); 3.22 (s, 3 H, 16-OMe); 3.54 (s, 3 H, 2-OMe); 3.62 (m, 2 H, 19-H, 25-H); 3.68 (m, 2 H, 21-H, 7-H); 3.86 (dd, J=9, 1 H, 16-H); 3.91 (m, 1 H, 32-H); 5.12 (dd, J=9, 1, 1 H, 17-H); 5.15 (dd, J=15, 9, 1 H, 15-H); 5.23 (ddq, J=15, 8, 1, 1 H, 26-H); 5.58 (dq, J=15, 6.5, 1 H, 27-H); 5.68 (d, J=10, 1 H, 5-H); 5.76 (d, J=11, 1 H, 13-H); 6.42 (s, 1 H, 3-H); 6.60 (dd, J=14, 11, 1H, 14-H) ppm.

$^{13}$C-NMR (125 MHz, $CD_2Cl_2/CD_3OD$ 2:1, −20° C.): $\delta_C$=8.3 (20-Me); 9.9 (18-Me); 12.2 (8-ethyl-$CH_3$); 14.5 (4-Me); 14.9 (24-Me); 16.6 (12-Me); 17.3 (6-Me); 18.0 (28-M); 22.0 (10-Me); 23.3 (8-ethyl-$CH_2$); 34.9 (C-22); 35.7 (C-6); 36.2 (C-10); 38.2 (C-18); 39.8 (C-24, C-20); 44.7 (C-8); 46.2 (C-11); 6.1 (16-OMe); 59.7 (2-OMe); 63.2 (C-23); 70.0 (C-19); 73.6 (C-7); 74.2 (C-21); 76.5 (C-17); 79.9 (C-25); 80.0 (C-9); 83.1 (C-16); 123.6 (C-13); 127.4 (C-15); 129.5 (C-27); 131.2 (C-26); 131.7 (C-3); 132.2 (C-4); 134.3 (C-14); 141.7 (C-5); 142.5 (C-2); 143.4 (C-12); 166.8 (C-1) ppm.

EXAMPLE 22

21,23-Dideoxy-23-epichloroconcanolide A

A mixture of 92.7 mg (0.14 mmol) of 21-deoxyconcanolide A and 61.4 mg (0.23 mmol, 1.6 equiv.) of triphenylphosphine in 20 ml of $CCl_4$ is stirred at 100° C. for 24 hours. The reaction mixture is cooled to room temperature and the solvent is then removed using a rotary evaporator and the residue is separated by column chromatography (silica gel, eluant: EtOAc/hexane 1:2). 22.1 mg of chloride (43% of the conversion) and 43.2 mg of starting material are obtained.

M.p.: 100° C.

$C_{39}H_{63}O_8Cl$ (695.37)

$R_f$=0.47 (system G)

FAB-MS (positive ions): m/e=694/696 [$M^+$], 716/718 [$M^+$+Na]

IR: ν=3505, 2966, 2875, 1695, 1453, 1358, 1248, 1104, 1005, 967, 762 $cm^{-1}$

UV (MeOH): $\lambda_{max}$ (ε)=244 (35 100); 283 nm (15 600)

$[\alpha]^{20}_D$=18.5 (c=0.59 MeOH)

$^1$H-NMR (500 MHz, $CD_2Cl_2/CD_3OD$ 2:1, −20° C.): $\delta_H$=0.82 (m, 12 H, 24-Me, 18-Me, 20-Me, 8-ethyl-$CH_3$); 0.99 (d, J=7, 3 H, 6-Me); 1.02 (d, J=7, 10-Me); 1.11 (m, 2 H, 8-ethyl-$CH_2$); 1.43 (ddt, J=11, 8, 3, 1 H, 8-H); 1.60 (dd, J=6.5, 1.5, 3 H, 28-Me); 162 (m, comp, 1 H, 20-H); 1.68 (ddq, J=10, 6.5, 3, 1 H, 24-H); 1.76 (m, 1 H, 22β-H); 1.88 (s, 3 H, 12-Me); 1.93 (m, comp, 2 H, 11-$CH_2$); 1.94 (s, 3 H, 4-Me); 2.04 (m, 1 H, 18-H); 2.13 (dd, J=14, 5, 1 H, 22α-H); 2.40 (m, 1 H, 10-H); 2.67 (m, 1 H, 6-H); 3.12 (d, J=10.5, 1 H, 9-H); 3.22 (s, 3 H, 16-OMe); 3.52 (s, 3 H, 2-OMe); 3.64 (dd, J=10.5, 1.5, 1 H, 19-H); 3.68 (dd, J=10, 2.5, 1 H, 7-H); 3.81 (dd, J=10, 8, 1 H, 25-H); 3.86 (dd, J=9, 1 H, 16-H); 3.91 (dr, J=10, 1, 1 H, 21-H); 4.47 (n, 1 H, 23-H); 5.14 (dd, J=9, 0.5, 1 H, 17-H); 5.15 (dd, J=15, 9, 1 H, 15-H); 5.26 (ddq, J=15, 8, 1, 1 H, 26-H); 5.60 (dq, J=15, 6, 1 H 27-H); 5.68 (d, J=10, 1 H, 5-H); 5.80 (d, J=11, 1 H, 13-H); 6.42 (s, 1 H, 3 H); 6.62 (dd, J=15, 11, 1 H, 14-H) ppm.

$^{13}$C-NMR (125 MHz, $CD_2Cl_2/CD_3OD$ 2:1, −20° C.): $\delta_C$=8.3 (20-Me); 9.8 (18-Me); 12.0 (8-$CH_2$-$\underline{C}H_3$); 14.3 (4-Me); 15.7 (24-Me); 16.5 (12-Me); 17.1 (6Me); 18.0 (28-Me); 21.8 (6-Me);18 (10-Me); 23.1 (8$\underline{C}H_2$-$CH_3$); 35.4 (C.6); 36.3 (C-10); 38.0 (C-18); 38.9 (C-22); 39.4 (C-20); 40.5 (C-24); 44.4 (C-8); 45.8 (C-11); 56.0 (16-OMe); 59.7 (2-OMe); 65.0 (c-23); 69.9 (C-19); 73.0 (C-21); 74.2 (C-7); 76.4 (C-17); 78.8 (C-25); 79.8 (C-9); 82.9 (C-16); 123.4 (C-13); 127.2 (C-15); 129.5 (C-27); 130.8 (C-26); 131.5 (C-3); 132.1 (C-4); 134.0 (C-14); 141.3 (C-5); 142.3 (C-2); 143.0 (C-12); 166.6 (C-1) ppm.

EXAMPLE 23

Oxidation of 21-deoxyconcanolide A to 21-deoxyconcanolide A-23-ketone 138 mg of 21-deoxyconcanolide A (0.20 mmol) are dissolved in 20 ml of dry $CH_2Cl_2$ and 87.5 mg (0.65 mmol, 3.25 equiv.) of 4-methylmorpholine 4-oxide monohydrate and 6.2 mg (0.02 mmol, 0.1 equiv.) of tetrapropylammonium perruthenate are added and the reaction mixture is stirred for 2 hours at room temperature. The reaction mixture is separated, without further working-up, by chromatography on silica gel (eluant: EtOAc/hexane, 1:1) to yield 45.2 mg of 21-deoxyconcanolide A-9,23-diketone (39% of the conversion), 20.9 mg of 21-deoxyconcanolide A-23-ketone (17% of the conversion) and 16 mg of starting material.

The product spectrum can be controlled by varying the reaction temperature. At 0° C. only 21-deoxyconcanolide A-23-ketone is obtained, in a low yield (<20%), at room temperature 21-deoxyconcanolide A-9,23-diketone is additionally obtained, without the yield of 21-deoxyconcanolide A-23-ketone increasing.

21-Deoxyconcanolide A-23-Ketone

M.p.: 98° C.

$C_{39}H_{62}O_9$ (674.91)

$R_f$=0.57 (system F)

FAB-MS (positive ions): m/e=696 [$M^+$+Na]

IR: ν=3451, 2969, 2931, 1709, 1621, 1455, 1356, 1248, 1103, 967 $cm^{-1}$

UV (MeOH): $\lambda_{max}$ (ε)=245 (26 200); 282 nm (11 500)

$[\alpha]^{20}_D$=+3.7 (c=0.27 MeOH)

$^{13}$H-NMR (500 MHz, $CD_2Cl_2/CD_3OD$ 2:1, −20° C.): $\delta_H$=0.83 (m, 12 H, 20-Me, 18-Me, 20-Me, 8-ethyl-$CH_3$); 0.99 (d, J=7, 3 H, 6-Me); 1.02 (d, J=7, 3 H, 10-Me); 1.10 (m, 2 H, 8-ethyl-$CH_2$); 1.42 (m, 1 H, 8-H); 1.63 (dr, J=6.5, 1.5, 3 H, 28-Me); 1.80 (m, 1 H, 20-H); 1.89 (s, 3 H, 12-Me); 1.94 (s, 3 H, 4-Me); 2.00–2.09 (m, 3 H, 18-H, 11-$CH_2$); 2.31 (m, 2 H, 24-H, 22β-H); 2.40 (m, 1 H, 10-H); 2.52 (dd, J=9, 2.5, 1 H, 22α-H); 2.68 (m, 1 H, 6-H); 3.12 (d, J=10, 1 H, 9-H); 3.22 (s, 3 H, 16-OMe); 3.53 (s, 3 H, 2-OMe); 3.59 (dd, J=11, 8, 1 H, 25-H); 3.67 (m, 3 H, 7-H, 19-H, 21-H); 3.87 (dd, J=9, 1 H, 16-H); 5.12 (dd, J=9, 1, 1 H, 17-H); 5.15 (dr, 15, 9, 1 H, 15-H); 5.40 (ddq, J=10, 6.5, 2, 1 H, 27-H); 5.63 (dq, J=15, 6.5, 1 H, 26-H); 5.69 (d, J=10, 1 H, 13-H); 5.76 (d, J=11, 1 H, 5-H); 6.42 (s, 1 H, 3-H); 6.63 (d, J=15, 11, 1 H, 14-H) ppm.

$^{13}$C-NMR (125 MHz, $CD_2Cl_2/CD_3OD$ 2:1, −20° C.): $\delta_C$=7.8 (20-Me); 9.7 (24-Me, 18-Me); 12.0 (8-ethyl-$CH_3$); 14.4 (4-Me); 16.4 (12-Me); 17.2 (6-Me); 18.0 (28-Me) 22.0 (10-Me; 23.0 (8-ethyl-$CH_2$); 35.4 (C-6); 36.0 (C-10); 37.7 (C-18): 40.6 (C-20); 44.3 (C-8); 46.0 (C-11); 46.7 (C-22); 50.4 (C-24); 56.0 (16-OMe); 59.6 (2-OMe); 69.7 (C-19); 73.8 (C-21); 76.3 (C-17); 78.7 (C-7); 79.8 (C-9); 82.6 (C-16); 84.6 (C-25); 123.3 (C-13); 127.0 (C-15); 130.1 (C-26); 130.6 (C-27); 131.7 (C-3); 132.0 (C-4); 134.6 (C-14); 141.6 (C-5); 142.1 (C-12); 143.3 (C-2); 166.8 (C-1); 210.7 (C-23) ppm.

21-Deoxyconcanolide A-9,23-diketone

M.p.: 100° C.

$C_{39}H_{60}O_9$ (672.90)

$R_f$=0.71 (system F)

FAB-MS (positive ions): m/e=694 [$M^+$+Na]

IR: ν=3454, 2970, 2932, 1701, 1623, 1454, 1357, 1248, 1104, 968 $cm^{-1}$

UV (MeOH): $\lambda_{max}$ (e)=244 (34 400); 278 nm (15 100)

$[\alpha]^{\circ}_D$=−53.75 (c=0.4 MeOH)

$^1$H-NMR (500 MHz, $CD_2Cl_2/CD_3OD$ 2:1, −20° C.): $\delta_H$=0.71 (t, J=7,3H, 8-ethyl-$CH_3$); 0.81 (d, J=7, 3 H, 18-Me); 0.84 (d, J=7, 3 H, 24-Me); 0.85 (d, J=7, 3 H, 20-Me); 0.97 (d, J=7, 3 H, 6-Me); 1.09 (d, J=7, 3 H, 10-Me); 1.11 (m, comp, 1 H, 8-ethyl-$CH_2$, β-H); 1.44 (ddt, J=13.5, 11, 7, 1 H, 8-ethyl-$CH_2$, α-H); 1.64 (dd, J=6.5, 1.5, 3 H, 28-Me); 1.80 (m, 1 H, 20-H); 1.94 (s, 3 H, 12-Me); 1.97 (s, 3 H, 4-Me); 2.05 (m, 1 H, 18-H); 2.31 (m, 3 H, 24-H, 22β-H, 1113-H); 2.42(dd, J=16,8, 1 H, 11α-H); 2.52(dd, J=14, 2.5, 1 H, 22α-H); 2.61 (ddd, J=10, 7, 2.5, 1 H, 6-H); 2.78 (dd, J=10, 2.5, 1 H, 8-H); 2.93 (m, 1 H, 10-H); 3.24 (s, 3 H, 16-OMe); 3.45 (dd, J=10, 2.5, 1 H, 19-H); 3.55 (s, 3 H, 2-OMe); 3.60 (m, 2 H, 21-H, 25-H); 3.67 (m, 1 H, 7-H); 3.89 (dd, J=9, 1 H, 16-H); 5.19 (dd, J=9, 1, 1 H, 17-H); 5.24 (dd, J=14.5, 9, 1 H, 25-H); 5.41 (ddq, J=15, 8, 1.5, 1 H, 26-H); 5.63 (dq, J=15, 6.5, 1 H, 27-H); 5.73 (d, J=9.5, 1 H, 5-H); 5.93 (d, J=10.5, 1 H, 13 H); 6.50 (s 1, H, 3-H); 6.67 (dd, J=15, 11, 1 H, 14-H) ppm.

$^{13}$C-NMR (125 MHz, $CD_2Cl_2/CD_3OD$ 2:1, −20° C.): $\delta_C$=7.8 (20-Me); 9.7 (24Me); 9.8 (18-Me); 12.2 (8-ethyl-$CH_3$); 14.4 (4-Me); 15.9 (12-Me); 16.5 (6-Me); 18.0 (10-Me, 28-Me); 20.8 (8-ethyl-$CH_2$); 35.4 (C-6); 37.8 (C-18); 40.5 (C-20); 42.0 (C-11); 46.0 (C-10); 46.7 (C-22); 50.4 (C-24); 54.2 (C-8); 56.0 (16-OMe); 59.7 (2-OMe); 69.6 (c-7); 75.9 (C-19); 76.2 (C-17); 78.7 (C-21); 82.7 (C-16); 84.5 (C-25); 124.7 (C-13); 127.8 (C-15); 130.0 (C-27); 130.5 (C-26); 131.6 (C-3); 133.0 (C-4); 133.9 (C-14); 140.0 (C-5); 141.5 (C-2); 142.3 (C-12); 166.5 (C-1); 210.6 (C-23); 218.1 (C-9) ppm.

What is claimed is:

1. A method for using a compound of formula (I)

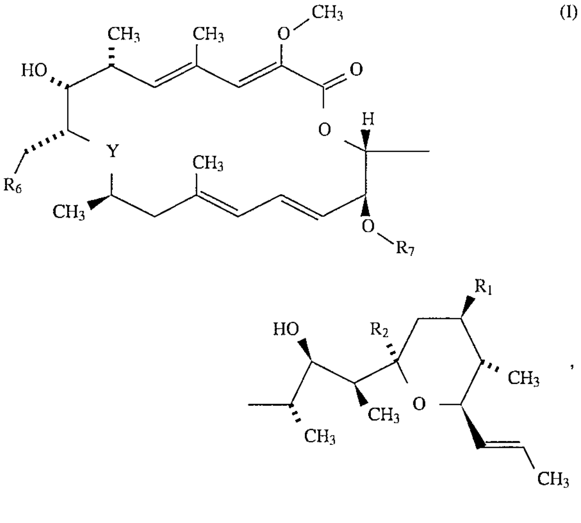

, wherein $R_1$ is hydroxy, 2-hydroxyethoxy, $C_1$–$C_4$alkoxy, $C_1$–$C_4$alkanoyloxy, halogen, amino, azido, a keto, p-nitrobenzenesulfonyl or a pyranyloxy group of the formula

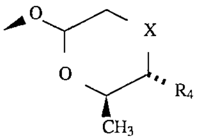

wherein

X is a group of the formula

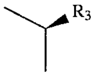 or 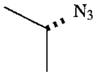

wherein $R_3$ is hydroxy, $C_1$–$C_4$alkanoyloxy or organic sulfonyloxy, and $R_4$ is hydroxy, $C_1$–$C_4$alkanoyloxy or carbamoyloxy, $R_2$ is hydrogen, hydroperoxy, hydroxy or $C_1$–$C_4$alkoxy, Y is a group of the formula

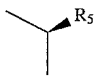 or 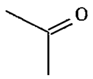

wherein $R_5$ is hydroxy or $C_1$–$C_4$alkanoyloxy, and $R_6$ and $R_7$ are each independently of the other hydrogen or methyl, comprising preparing of a medicament that is suitable for the prophylaxis and treatment of diseases that respond to the inhibition of the osteoclast proton pump.

2. The method of claim 1 wherein $R_1$ is hydroxy, methoxy, $NH_3$, chlorine, bromine, a keto, p-nitrobenzenesulfonyl or a pyranyloxy group of the formula

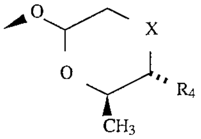

wherein $R_4$ is hydroxy, acetoxy, or carbamoyloxy and

X is a group of the formula

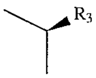 or 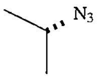

wherein $R_3$ is hydroxy, acetoxy or benzenesulfonyloxy that is unsubstituted or mono-substituted by $C_1$–$C_4$alkyl, halogen or by nitro, $R_2$ is hydrogen or hydroxy, Y is a group of the formula

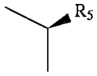 or 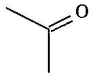

wherein $R_5$ is hydroxy or acetoxy and $R_6$ is methyl.

3. The method of claim 1 wherein $R_1$ is hydroxy, methoxy, $NH_3$, chlorine, a keto, or a pyranyloxy group of the formula

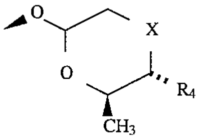

wherein $R_4$ is hydroxy or carbamoyloxy and

X is a group of the formula

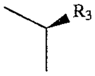

wherein $R_3$ is hydroxy or acetoxy, $R_2$ is hydrogen or hydroxy, and

Y is a group of the formula

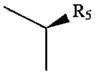

and $R_5$ is hydroxy or acetoxy.

4. The method of claim 1 wherein said formula (I) is concanamycin A.

5. The method of claim 1 wherein said formula (I) is concanolide A.

6. The method of claim 1 wherein said formula (I) is concanamycin B.

7. The method of claim 1 wherein said formula (I) is concanolide B.

8. The method of claim 1 wherein said formula (I) is concanamycin C.

9. The method of claim 1 wherein said formula (I) is 21-deoxy-concanolide A.

10. The method of claim 1 wherein said formula (I) is 21-deoxy-concanolide B.

11. The method of claim 1 wherein said formula (I) is 23-O-methyl-concanolide A.

12. The method of claim 1 wherein said formula (I) is 3',9-di-O-acetyl-concanamycin A.

13. The method of claim 1 wherein said form 16-demethyl-21-deoxyconcanolide A, 21,23-dideoxy-23-epiazidoconcanolide A, 23-O-(p-nitrobenzenesulfonyl)-21-deoxyconcanolide A, 21-deoxyconcanolide A-23-ketone, 21-deoxyconcanolide A-9,23-diketone and/or 21,23-dideoxy-23-epichloroconcanolide A.

14. A compound of formula

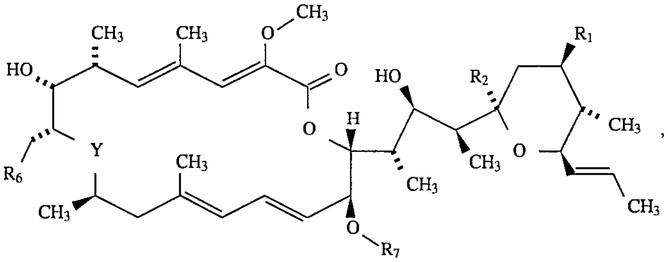

, (I)

wherein $R_6$ and $R_7$ are each independently of the other hydrogen or methyl, and wherein R is hydroxy, halogen, amino, azido, p-nitrobenzenesulfonyl or keto, $R_2$ is hydrogen and Y is a group of the formula

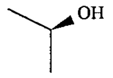

or wherein R is halogen, amino, azido, keto, p-nitrobenzenesulfonyl or a pyranyloxy group of the formula

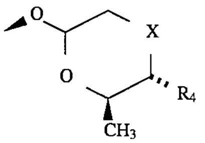

wherein $R_4$ is carbamoyloxy and X is a group of the formula

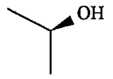

$R_2$ is hydroxy and Y is group of the formula

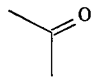

or wherein $R_1$ is halogen, amino, azido, 2-hydroxyethoxy, a keto, p-nitrobenzenesulfonyl or a pyranyloxy group of the formula

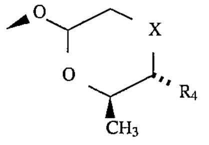

wherein $R_4$ is hydroxy or carbamoyloxy and X is a group of the formula

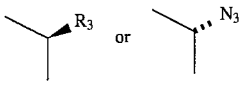

wherein $R_3$ is benzenesulfonyloxy that is unsubstituted or monosubstituted by $C_1$–$C_4$alkyl, halogen or by nitro, $R_2$ is hydrogen, bydroperoxy or hydroxy and Y is a group of the formula

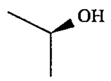

or wherein $R_1$ is halogen, amino, azido, a keto group, p-nitrobenzinesulfonyl, $C_1$–$C_4$alkoxy or $C_1$–$C_4$alkanoyloxy, $R_2$ is hydroxy or $C_1$–$C_4$alkoxy, and Y is a group of the formula

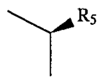

and $R_5$ is $C_1$–$C_4$alkanoyloxy.

15. A compound of formula (I) according to claim 14 wherein $R_1$ is hydroxy, azido or chlorine, $R_2$ is hydrogen and Y is a group of the formula

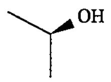

or $R_1$ is a pyranyloxy group of the formula

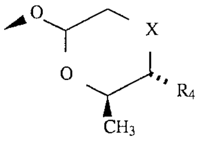

wherein $R_4$ is carbamoyloxy and X is a group of the formula

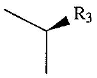

or

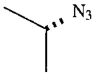

wherein $R_3$ is benzenesulfonyloxy monosubstituted by nitro, $R_2$ is hydroxy and Y is a group of the formula

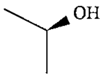

or $R_1$ is acetoxy, $R_2$ is hydroxy and Y is a group of the formula

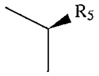

and $R_5$ is acetoxy.

16. 21-Deoxy-concanolide A according to claim 14.

17. 16-Demethyl-21-deoxyconcanolide A according to claim 14.

18. 21,23-Dideoxy-23-epiazidoconcanolide A according to claim 14.

19. 21,23-Dideoxy-23-epichloroconcanolide A according to claim 14.

20. 23-O-(p-nitrobenzenesulfonyl)-21-deoxyconcanolide A according to claim 14.

21. 21-Deoxyconcanolide A-23-ketone according to claim 14.

22. 21-Deoxyconcanolide A-9,23-diketone according to claim 14.

23. A pharmaceutical composition comprising a compound of formula (I) according to claim 14.

24. A method for the prophylactic or therapeutic treatment of a human or animal body comprising treating said human or animal body with the compound of claim 14.

* * * * *